United States Patent [19]

Assi et al.

[11] Patent Number: 4,927,754

[45] Date of Patent: May 22, 1990

[54] METHOD FOR SELECTIVELY INCREASING THE RATIO OF SINGLE MAJOR COMPONENTS OF TEICOPLANIN A2 COMPLEX

[75] Inventors: Francesco Assi, Cernusco Sul Naviglio; Giancarlo Lancini, Pavia; Anacleto Gianantonio, Milan, all of Italy

[73] Assignee: Gruppo Lepetit S.p.A., Milan, Italy

[21] Appl. No.: 864,675

[22] Filed: May 19, 1986

[30] Foreign Application Priority Data

May 21, 1985 [GB] United Kingdom ............... 8512795

[51] Int. Cl.$^5$ .................... C12P 19/56; C12P 21/04; C12N 1/38
[52] U.S. Cl. ................................ 435/71.3; 435/78; 435/827; 435/244; 435/169
[58] Field of Search ............ 435/71, 74, 169, 244, 435/822, 827

[56] References Cited

U.S. PATENT DOCUMENTS 4,239,751  12/1980  Coronelli .................... 435/169

FOREIGN PATENT DOCUMENTS 0204179  12/1986  European Pat. Off. .
2121401  12/1983  United Kingdom ............ 435/71

Primary Examiner—Charles F. Warren
Assistant Examiner—Irene Marx

[57] ABSTRACT

The object of this invention is to provide a method for selectively increasing the ratio of the single T-A2 major components in the T-A2 complex. More particularly, the object of this invention is a process for obtaining teicoplanin A$_2$ selectively enriched in any of its major components, T-A2-1, T-A2-2, T-A2-3, T-A2-4 and T-A2-5 which consists in adding to the culture medium of *Actinoplanes teichomyceticus* nov. sp. ATCC 31121 or a mutant thereof which produces T-A2 complex through the same metabolic pathway, a selectively effective amount of an appropriate precursor.

49 Claims, No Drawings

METHOD FOR SELECTIVELY INCREASING THE RATIO OF SINGLE MAJOR COMPONENTS OF TEICOPLANIN A2 COMPLEX

Teicoplanin (formerly named teichomycin) is a glycopeptide antibiotic produced by cultivating *Actinoplanes teichomyceticus* nov. sp. ATCC 31121. This antibiotic is active mainly against infections by gram-positive bacteria.

According to the procedure described in U.S. Pat. No. 4,239,751, teicoplanin is isolated from the fermentation broths of the producing strain as a complex containing three factors named $A_1$, $A_2$ and $A_3$. Factor $A_2$ is present in preponderant amount in the antibiotic complex recovered from the fermentation of the above strain and is the most important for its biological effects. Factor $A_1$ and factor $A_3$ are present only in minor amount.

According to U.S. Pat. No. 4,239,751, teicoplanin $A_2$ (T-A2) is isolated from the other factors of teicoplanin complex by column chromatography on Sephadex® LH-20, which is a hydroxypropyl derivative of a crosslinked polydextran gel with an exclusion limit at about molecular weight 4.000.

From large scale preparation and purification operations (examples of these operations are given in European Patent Application Publication No. 0122969) it is usually obtained a teichomycin product essentially consisting of teicoplanin $A_2$ accompanied by a small quantity of teicoplanin $A_3$. This product is suitable for practical use in therapeutical applications. See: Drugs of the Future: Vol. 9, No. 6, 1984, pages 429–430 edited by J. R. Prous Publishers, Barcelona, Spain.

A paper published by A. Borghi, C. Coronelli et al. in Journal of Antibiotics Vol. 37, No. 6 pp. 615–620, Jun. 1984, teaches that teicoplanin factor $A_2$ (T-A2) is, in turn, a mixture of five closely related major components of very similar polarity.

These components, designated as T-A2-1, T-A2-2, T-A2-3, T-A2-4 and T-A2-5, were isolated by using, in a first step, reverse phase partition chromatography at normal pressure on a silanized silica gel column. The purification of components T-A2-3, T-A2-4 and T-A2-5 required a further step with the application of semi-preparative HPLC on a Whatman Partisil® ODS M-9 column eluted with a 0.2% aqueous ammonium formate-acetonitrile mixture (76:24). All said components have been chemically and biologically characterized. See also British patent application publication No. 2,121,401.

Structural elucidations reported by J. C. J. Barna, D. M. Williams et al. in J. Am. Chem. Soc. 1984, 106, 4895–4902, show that the teicoplanin $A_2$ major components may be represented by the following structural formula:

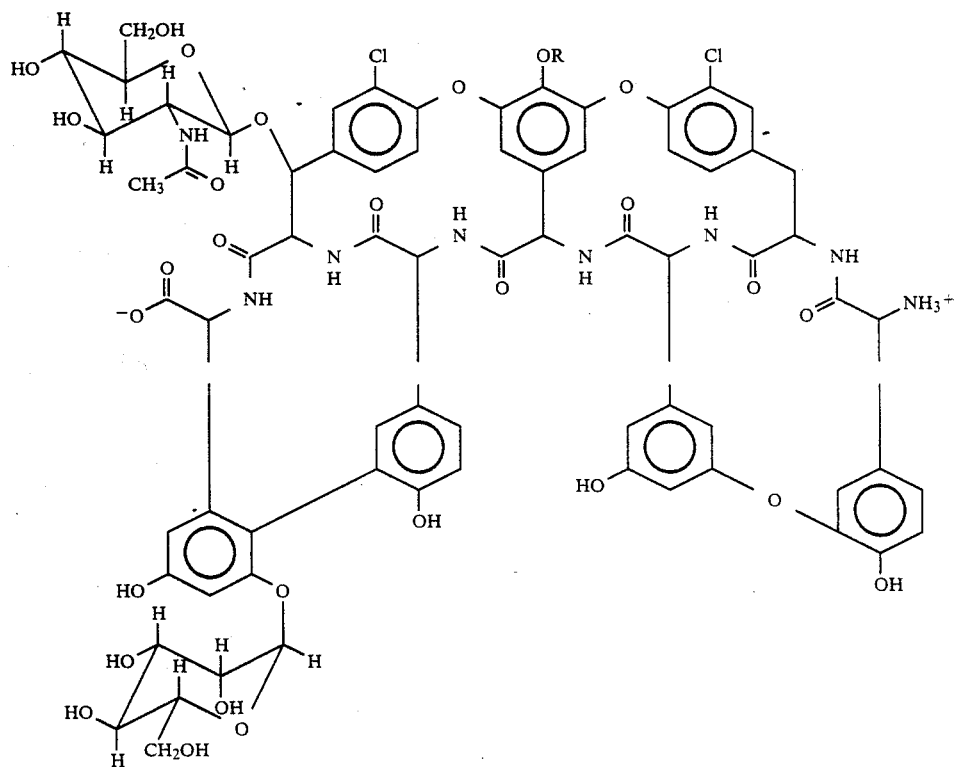

where:

T-A2-1: R' = —CO—(CH$_2$)$_2$—CH=CH—(CH$_2$)$_4$—CH$_3$   ((Z)-4-decenoyl)

T-A2-2: R' = —CO—(CH$_2$)$_6$—CH(CH$_3$)$_2$   (8-methylnonanoyl)

T-A2-3: R' = —CO—(CH$_2$)$_8$—CH$_3$   (n-decanoyl)

T-A2-4: R' = 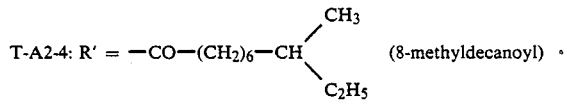   (8-methyldecanoyl)

T-A2-5: R' = —CO—(CH$_2$)$_7$—CH(CH$_3$)$_2$   (9-methyldecanoyl)

In vitro and in vivo tests reported in the above mentioned British patent application publication No. 2,121,401, show that each of the T-A2-2, T-A2-3, T-A2-4 and T-A2-5 components is more active than the teicoplanin A$_2$ complex as a whole.

It is therefore apparent that a method for selectively enhancing the production of each of the major components of teicoplanin A$_2$ is a primary objective in teicoplanin industrial fermentation. The significative technical advantage it may offer concerns both the purpose of isolating the single T-A2 major components in a pure form and the possibility of obtaining a T-A2-complex enriched with the more active components. Moreover, the possibility of modulating the ratio of the single T-A2 major components in the T-A2 complex in the large scale industrial fermentation, offers a useful tool to maintain constant the composition of the fermentation product which must adhere to standard specifications. In other words, when for any reason (e.g., a modification of the industrial culture medium to employ less expensive materials), the percent composition of the single components tends to depart from that of the standard, the possibility of selectively increasing each of the T-A2 major components offers a useful tool to correct such a defect.

The object of this invention is to provide a method for selectively increasing the ratio of the single T-A2 major components in the T-A2 complex. More particularly, the object of this invention is a process for obtaining teicoplanin A$_2$ selectively enriched in any of its major components T-A2-1, T-A2-2, T-A2-3, T-A2-4 and T-A2-5 which consists in adding to the culture medium of *Actinoplanes teichomyceticus* nov. sp. ATCC 31121 or a mutant thereof which produces T-A2 complex through the same metabolic pathway, a selectively effective amount of an appropriate precursor of the characteristic acyl group linked to a glucosamine moiety of T-A2 (see the above meanings for R'), hereinafter: "appropriate precursor of the respective acyl group of the glucosamine moiety of T-A2".

The process of this invention is characterized in that:

(a) the appropriate precursor for increasing the ratio of T-A2-1 in T-A2 complex is selected from linoleic acid, its salts with bases which are non-toxic to the microorganism and its esters with mono- and poly-hydroxy lower alkanols (b) the appropriate precursor for increasing the ratio of T-A2-2 in T-A2 complex is selected from valine, its salts with acid and bases which are non-toxic to the microorganism, alpha-keto-isovaleric acid, its salts with bases which are non-toxic to the microorganism, is esters with mono- and poly-hydroxy lower alkanols, isobutyric acid, its salts with bases which are non-toxic to the microorganism, its esters with mono- and poly-hydroxy lower alkanols, isobutanol and its esters with acids which are non-toxic to the microorganism (c) the appropriate precursor for increasing the ratio of T-A2-3 in T-A2 complex is selected from oleic acid, its salts with bases which are non-toxic to the microorganism, its esters with mono- and poly-hydroxy lower alkanols (d) the appropriate precursor for increasing the ratio of T-A2-4 in T-A2 complex is selected from isoleucine, its salts with acids and bases which are non-toxic to the microorganism, alpha-keto-beta-methylvaleric acid, its salts with bases which are non-toxic to the microorganism, its esters with mono- and poly-hydroxy lower alkanols, 2-methylbutyric acid, its salts with bases which are non-toxic to the microorganism, its esters with mono- and poly-hydroxy lower alkanols, 2-methylbutanol and its esters with acids which are non-toxic to the microorganism (e) the appropriate precursor for increasing the ratio of T-A2-5 in T-A2 complex is selected from leucine, its salts with acids and bases which are non-toxic to the microorganism, isovaleric acid, its salts with bases which are non-toxic to the microorganism, its esters with mono- and poly-hydroxy lower alkanols, alpha-keto-isocaproic acid, its salts with bases which are non-toxic to the microorganism, its esters with mono- and poly-hydroxy lower alkanols, isoamyl alcohol and its esters with acids which are non-toxic to the microorganism.

Salts with bases which are non-toxic to the microorganism are salts wherein the type and concentration of the given cation is such that it does not impair the growth of the microorganism culture or the production of the desired antibiotic substance to a considerable extent. Examples of said cations are sodium, potassium, ammonium and the like.

Esters with mono- and poly-hydroxy lower alkanols are (C$_1$–C$_6$)alkanols with 1, 2, 3, 4, 5 or 6 hydroxy functions per molecule.

When (C$_4$–C$_6$)alkanols are used, they must be different from those which act as precursors for other T-A2 major components (e.g. isobutanol, isoamyl alcohol, and 2-methylbutanol) unless concomitant increase of one or more of said components is desired.

Preferred examples of poly-hydroxy alkanols are glycerol and propylene glycol.

When the lower alkanol is present in different enantiomeric and epimermic forms, in the present description and claims, both each single form separately and the mixture of the single forms in any proportion are intended.

Esters which are non-toxic to the microorganism are (C$_2$–C$_{22}$)alkanoyl esters wherein the type and concentration of the alkanoyl moiety in the fermentation medium is such that it does not impair the growth of the microorganism culture or the production of the desired antibiotic substance to a considerable extent. In general, straight chain ($C_2$–$C_4$)alkanols are preferred.

The method of this invention involves cultivating the above mentioned strain in an aqueous nutrient culture medium containing an assimilable source of carbon, an assimilable source of nitrogen and inorganic salts under the usual conditions described in the prior-art for the production of teicoplanin, with the improvement that a selectively effective amount of an appropriate precursor is added to the fermentation medium before inoculation of the strain or during the fermentation process to selectively increase the production of one or more the teicoplanin $A_2$ components T-A2-1, T-A2-2, T-A2-3, and T-A2-4 and T-A5.

The expression "a mutant thereof which produces T-A2 complex through the same metabolic pathway" refers to those natural or artificial mutants of *Actinoplanes teichomyceticus* ATCC 31121 (parent strain) which produce the T-A2 complex by using essentially the same enzymatic systems as the parent strain to provide the R' fatty acyl moiety of the T-A2 complex.

In this specification and in the claims the expression "selectively effective amount" means a quantity of selective precursor which, when added to the culture medium, yields a concentration of selective precursor sufficient to produce the selective increase of a specific component of T-A2 complex without causing toxic effects to the microorganism.

The nutrient fermentation media suitable for the fermentation of T-A2 producing strain which can be used in the embodiment of this invention usually contain: a suitable carbon source which, for instance, may be selected from sugars (e.g. glucose, sucrose, maltose), polysaccharides (e.g. starch, dextrane) polyalcohols (e.g. glycerol, propylene glycol); a suitable nitrogen source which, for instance, may be selected from ammonium salts, asparagine, peanut meal, soybean meal, meat extract, tryptone, peptone, yeast hydrolyzate, yeast extract and corn step liquor; acid mineral salts such as sodium chloride, calcium carbonate, magnesium sulfate.

The fermentation is carried out for a time varying from 50 to 200 hours under aerobic conditions at a temperature between 25° C. and 35° C., preferably between 27° C. and 33° C. The addition of the selectively effective amount of appropriate precursors can be made to the fermentative media before inoculation of the producing strain, however, it is preferably made 24 to 48 hours after the fermentation is started. The addition may be made in one or several portions or in a continuous way.

According to a typical experiment embodying this invention, the *Actinoplanes teichomyceticus* strain maintained on oat-meal agar slants is inoculated into a flask containing 100 ml of vegetative medium. After 36 hours, samples of the culture (5 milliliters) are used to inoculate a series of fermentation flasks containing 100 ml of fermentative medium. After 24 to 48 hours of fermentation the selectively effective amount of precursor is added as appropriate. If concomitant increase of two or more major components of T-A2 complex is desired, two or more precursors can be added to the same fermentation flask. The fermentation is continued for additional 60 to 150 hours, the medium is centrifugated off and samples of the broth are analyzed for T-A2 major components concentration by high performance liquid chromatography (HPLC).

The addition of the precursor is generally made in a way that may not alter the pre-determined pH value of the fermentation medium. Thus, for instance, when free acid precursors are added directly to the medium, the pH value is maintained under control by buffering the medium or by immediate neutralization with bases which are non-toxic to the microorganism.

When the precursor to be added is an aminoacid, it may be supplied to the fermentation medium as an aqueous solution of its salt with acids or bases which are not toxic to the producing microorganism, e.g. hydrochlorides and sodium salts. Both racemic mixtures and optically active isomers can be used as precursors.

However, at least in some instances, the addition of the L-form gives higher yields than with the corresponding D-form.

A preferred embodiment of the process of this invention is represented therefore by the use of the L-aminoacid precursor for enhancing the concentration of T-A2-2 (valine, a salt or an ester thereof), T-A2-4 (L-isoleucine, a salt or an ester thereof) and/or T-A2-5 (L-leucine, a salt or an ester thereof) of teicoplanin $A_2$ complex. According to this preferred embodiment, it is also possible to increase the percentage of T-A2-2, T-A2-4 or T-A2-5 in the fermentation product up to 90–95% of the complex.

With lower alkanoic acid precursors (e.g. isobutyric acid, 2-methylbutyric acid, isovaleric acid, alpha-keto-isovaleric acid, alpha-keto-beta-methylvaleric acid, and alpha-keto-isocaproic acid) the addition may be made through an aqueous solution of their salts with non-toxic bases; ammonium and sodium salts are usually preferred.

When salts of unsaturated fatty acids, such as linoleic acid and oleic acid, are used as the appropriate precursor, sodium and ammonium salts are generally preferred. However, any salt with a base which is not toxic to the producing strain may be employed.

When esters of the above lower alkanoic acids and unsaturated fatty acids with mono-hydroxy lower alkanols are employed as precursors, said esters are usually derived from methanol, ethanol and propanol, although esters with $C_4$–$C_6$ alkanol must be different from those which may act as precursors for other T-A2 major components (e.g. isobutanol, isoamyl alcohol, and 2-methylbutanol) unless concomitant increase of one or more of said components is desired.

Preferred esters of the above lower alkanoic acid and unsaturated fatty acids with poly-hydroxy lower alkanols are the esters with ethylene glycol and glycerol, e.g. triisobutyrin, tri-oleine and tri-linoleine.

The addition of unsaturated fatty acids can be carried out also by using natural raw materials containing said acids as such or their glycerides. For instance, commercial soybean oil usually contains about 20 to about 35 percent of oleic acid and about 50 to about 60 percent of linoleic acids as triglycerides; lard contains about 40 to about 55 percent of oleic acid; cotton seed oil contains about 20 to about 45 percent of oleic acid and about 30 to about 55 percent of linoleic acid; sun flower seed oil contains about 15 to about 25 percent of oleic acid and about 65 to about 75 percent of linoleic acid.

Alkanol precursors such as isobutanol, isoamyl alcohol and 2-methylbutanol are usually added as such to the fermentation medium. However, they can be supplied also as esters of acids which are non-toxic to the microorganism. These acids must be different from those which may act as precursors for other T-A2 major components (e.g. isobutyric acid, isovaleric acid, 2-methylbutyric acid, linoleic acid, etc.) unless concomitant increase of one or more of said components is desired. Usually, esters with linear lower alkanoic acids such as acetic, propionic and butyric acid are preferred.

The "selectively effective amount" to be added to the fermentation medium according to this invention depends on the type of precursor. Usually, with the esters of the lower alkanoic acids (isobutyric acid, 2-methylbutyric acid, isovaleric acid) and the esters of unsaturated fatty acids (linoleic acid, oleic acid), amounts to yield a concentration into the fermentation medium ranging between 0.5 g/l and 15 g/l are employed with the range between 1 g/l and 5 g/l being preferred. With the lower alkanols (isobutanol, 2-methylbutanol, isoamyl alcohol) or their esters with acids which are non-toxic to the microorganism, amounts to yield a concentration ranging between 0.5 g/l and 5 g/l are usually employed, with the range between 1 g/l and 2 g/l being preferred.

With the aminoacids (e.g. valine, leucine, isoleucine) and the keto-acids (alpha-keto-isovaleric acid, alpha-keto-beta-methylvaleric acid, alpha-keto-isocaproic acid) or their salts with acids and bases the "selectively effective amount" added to the fermentation medium usually ranges between 0.5 g/l and 5 g/l, with the range between 1 g/l and 3 g/l being preferred.

In the case where the lower alkanoic acids (e.g. isobutyric acid, 2-methylbutyric acid, isovaleric acid), the unsaturated fatty acids (e.g. linoleic acid, oleic acid) or their salts are directly added to the fermentation medium, the "selectively effective amount" usually ranges between 0.1 g/l and 2.5 g/l, with the range between 0.3 g/l and 1.5 g/l being preferred. Higher concentrations are still effective in promoting the selective increase of the T-A2 major components but the overall yield of T-A2 complex is depressed because of toxic effects on the microorganism.

The following examples describe in detail some specific embodiments of this invention.

EXAMPLE 1

General Procedure

One oat meal agar slant of *Actinoplanes teichomyceticus* nov. sp. ATCC 31121 was inoculated into a 500 ml flask containing 100 ml of the following vegetative medium.

| | | |
|---|---|---|
| Glucose | 10 g/l | |
| Peptone Difco | 4 g/l | |
| Yeast extract | 4 g/l | |
| MgSO$_4$ | 0.5 g/l | |
| CaCO$_3$ | 5 g/l | |
| Standard oligo elements | 1 ml | of each of the solutions A, B and C |
| Water | 1000 ml | |
| (pH adjusted to 6.7 after sterilization) | | |

Solution A: 10% sodium chloride (w/v)
Solution B: 10% calcium chloride (w/v)
Solution C: H$_3$BO$_3$: 50 mg; CuSO$_4$: 4 mg; KI: 10 mg; FeCl$_3$: 20 mg; MgSO$_4$: 40 mg; FeSO$_4$: 40 mg; (NH$_4$)$_2$MoO$_4$: 20 mg; in 100 ml of distilled water.

After 36 hours of growth on a rotary shaker, five milliliters of the culture were used to inoculate the test flasks and standard flasks containing each 100 ml of fermentation medium having the following composition:

| | | |
|---|---|---|
| Yeast lisate | 5 g/l | |
| Asparagine | 1.5 g/l | |
| Glucose | 20 g/l | |
| MgSO$_4$ | 0.5 g/l | |
| CaCO$_3$ | 5 g/l | |
| Standard oligo elements | 1 ml | of each of the solutions A, B and C |
| Water | 1000 ml | |
| (pH adjusted to 6.9 after sterilization) | | |

Solutions A, B and C as above.

The fermentation was performed at 28°–30° C. on a rotary shaker. After 24 hours the appropriate precursor was added. The culture was centrifugated after 72 hours and samples 50 microliter of the broth were analyzed for the T-A2 major components concentration.

The analysis was performed according to the following HPLC method:

a. Separation by gradient reverse phase partition

| | |
|---|---|
| Instrument: | pump Varian 5000 A; detector Varian at 254 micrometer; injector: Rheodyne model 7125; integrator: Spectra Physics model 4000; |
| Column: | Zorbax ® ODS 5 micrometer, 4.6 × 150 mm; (Du Pont) |
| Mobile Phase: | (A) CH$_3$CN: 0.025 M NaH$_2$PO$_4$ 1:9, pH 6.0 (B) CH$_3$CN: 0.025 M NaH$_2$PO$_4$ 7:3, pH 6.0 |
| Gradient profile: | linear from 0% of B to 50% of B in 30 min. Flow rate 2 ml/min. |
| Injection: | 50 microliter of fermentation broth Retention times (minutes) T-A2-1 = 16.9 T-A2-2 = 18.0 T-A2-3 = 18.6 T-A2-4 = 20.5 T-A2-5 = 20.9 |
| Internal standard: | 3,5-dihydroxytoluene (r.t. 6.3 minutes). | b. Percentage distribution

The components were separated by the above procedure and their relative distribution was obtained as a percent of the total of the five peaks by the area percentage method.

| Additions g/l | Total yield microgram/l | T-A2-1 % | T-A2-2 % | T-A2-3 % | T-A2-4 % | T-A2-5 % |
|---|---|---|---|---|---|---|
| None | 340 | 2.0 | 30.4 | 18.1 | 26.1 | 23.3 |
| None | 305 | 2.1 | 32.0 | 20.6 | 20.1 | 25.0 |
| None | 379 | 1.8 | 32.9 | 20.4 | 24.1 | 20.7 |
| L-Valine (sodium salt) | | | | | | |
| 0.5 | 295 | 1.5 | 52.1 | 20.5 | 14.0 | 11.9 |
| 1 | 648 | 0.8 | 70.4 | 12.4 | 9.8 | 6.7 |
| 2 | 795 | 0.9 | 83.0 | 9.2 | 3.0 | 3.3 |
| L-Isoleucine (sodium salt) | | | | | | |
| 0.5 | 116 | 2.0 | 29.3 | 20.4 | 32.1 | 16.2 |
| 1 | 134 | 1.8 | 24.1 | 13.5 | 40.2 | 20.4 |
| 2 | 159 | 1.7 | 13.5 | 4.4 | 66.5 | 13.9 |
| L-Leucine (sodium salt) | | | | | | |
| 0.5 | 373 | 2.1 | 37.9 | 15.2 | 15.1 | 29.7 |
| 1 | 459 | 2.0 | 35.0 | 17.7 | 9.5 | 35.8 |
| 2 | 281 | 1.7 | 35.4 | 9.5 | 8.0 | 45.4 |
| 2.5 | 144 | 0.8 | 12.6 | 12.0 | 1.5 | 73.5 |
| L-valine (HCl) | | | | | | |
| 2.5 | 750 | 0.2 | 86.2 | 8.7 | 2.8 | 2.1 |
| Tri-oleine (containing 10% by-weight of tri-linoleine) | | | | | | |
| 2 | 320 | 12.0 | 17.2 | 41.0 | 18.9 | 10.9 |
| 4 | 258 | 12.3 | 16.1 | 48.8 | 16.9 | 10.9 |
| Tri-linoleine | | | | | | |
| 2 | 341 | 29.0 | 20.3 | 14.0 | 20.1 | 17.1 |

-continued

| Additions g/l | Total yield microgram/l | T-A2-1 % | T-A2-2 % | T-A2-3 % | T-A2-4 % | T-A2-5 % |
|---|---|---|---|---|---|---|
| 5 | 355 | 31.2 | 22.9 | 17.4 | 16.9 | 11.5 |

By operating according to the above procedure in a further set of experiments the following data were obtained.

| Additions g/l | Total yield microgram/l | T-A2-1 % | T-A2-2 % | T-A2-3 % | T-A2-4 % | T-A2-5 % |
|---|---|---|---|---|---|---|
| None | 460 | 2.2 | 44.1 | 20.8 | 15.2 | 17.7 |
| Isobutanol | | | | | | |
| 1 | 480 | 2.6 | 52.3 | 16.8 | 15.9 | 12.4 |
| 2 | 258 | 1.4 | 60.7 | 15.2 | 13.1 | 9.6 |
| 2-Methylbutanol | | | | | | |
| 1 | 423 | 2.3 | 42.1 | 15.2 | 26.3 | 14.1 |
| 2 | 265 | 1.7 | 46.3 | 10.5 | 30.1 | 11.4 |

EXAMPLE 2

General Procedure

*Actinoplanes teichomyceticus* nov. sp. ATCC 31121 was pre-cultivated in a 500 ml shake flask containing 100 ml of the following medium:

| | |
|---|---|
| Meat extract | 3 g/l |
| Tryptone | 5 g/l |
| Yeast extract | 5 g/l |
| Glucose | 1 g/l |
| Soluble starch | 24 g/l |
| Calcium carbonate | 5 g/l |
| Water | 1000 ml |
| (pH adjusted to 6.7 after sterilization) | |

The flasks were shaken for 24 hours at 28°–30° C. and then the pre-culture was used to inoculate jar fermentors each containing 10 liters of the following nutrient medium:

| | |
|---|---|
| Meat extract | 4 g/l |
| Peptone | 4 g/l |
| Yeast extract | 1 g/l |
| Sodium chloride | 2.5 g/l |
| Soybean meal | 10 g/l |
| Glucose | 50 g/l |
| Calcium carbonate | 5 g/l |
| Tap water q.s. | to 1000 ml |
| (pH adjusted to 6.9 after sterilization) | |

The fermentors were incubated aerobically under stirring for 24 hours then the appropriate precursor was added. The fermentation was continued for further 90 hours, then the fermentors were harvested. Samples of broth (100 ml) were filtered at pH 11 (the pH was adjusted by the addition of 20% (w/v) sodium hydroxide) and analyzed according to the procedure described under Example 1 by injecting 40 microliter of each filtered sample solution whose pH was adjusted to 7.38 with a 0.1M phosphate buffer.

| Additions g/l | Total yield microgram/l | T-A2-1 % | T-A2-2 % | T-A2-3 % | T-A2-4 % | T-A2-5 % |
|---|---|---|---|---|---|---|
| None | 678 | 4.5 | 50.9 | 16.0 | 15.8 | 12.8 |
| None | 684 | 3.5 | 50.0 | 15.1 | 17.0 | 14.4 |
| Tri-linoleine | | | | | | |
| 5 | 764 | 15.5 | 45.1 | 14.0 | 12.8 | 12.7 |
| 10 | 596 | 52.8 | 21.1 | 10.4 | 5.5 | 10.2 |
| Tri-oleine | | | | | | |
| 5 | 802 | 4.0 | 44.0 | 26.9 | 13.8 | 11.3 |
| 10 | 792 | 5.0 | 29.3 | 49.2 | 9.8 | 6.7 |
| Methyl ester of 2-methylbutyric acid | | | | | | |
| 1 | 720 | 2.8 | 40.3 | 15.2 | 31.0 | 10.7 |
| 3 | 846 | 4.2 | 40.9 | 11.9 | 35.7 | 7.3 |
| 5 | 530 | 5.7 | 41.3 | 9.6 | 37.2 | 6.2 |
| 2-Methylbutyric acid (sodium salt) | | | | | | |
| 0.5 | 531 | 3.8 | 39.6 | 14.6 | 32.3 | 9.7 |
| 1.5 | 357 | 5.0 | 35.9 | 10.6 | 41.4 | 7.1 |
| Methyl isobutyrate | | | | | | |
| 1 | 683 | 3.9 | 67.9 | 15.9 | 6.7 | 5.6 |
| 3 | 402 | 2.6 | 80.8 | 12.5 | 1.8 | 2.3 |
| 5 | 220 | 3.1 | 80.8 | 12.2 | 1.6 | 2.3 |
| Isobutyric acid (sodium salt) | | | | | | |
| 0.5 | 532 | 3.8 | 69.1 | 18.4 | 4.4 | 4.3 |
| 1.5 | 214 | 3.3 | 79.7 | 13.5 | 1.8 | 1.7 |
| L-Valine (buffered solution) | | | | | | |
| 1 | 458 | 2.3 | 79.3 | 10.2 | 4.3 | 3.9 |
| 2 | 377 | 3.2 | 83.9 | 9.4 | 1.6 | 1.9 |
| 3 | 250 | 1.9 | 85.3 | 9.6 | 1.2 | 2.0 |
| Cotton seed oil | | | | | | |
| 10 | 571 | 37.3 | 26.4 | 22.9 | 6.0 | 7.4 |
| Lard | | | | | | |
| 10 | 708 | 8.1 | 36.1 | 36.3 | 11.3 | 8.2 |
| Soybean oil | | | | | | |
| 10 | 637 | 39.9 | 23.8 | 21.6 | 7.4 | 7.3 |
| Sunflower oil | | | | | | |
| 10 | 712 | 31.7 | 31.8 | 18.6 | 8.8 | 9.1 |

For comparative purpose myristic acid, tripalmitin and tristearin were added to four jar fermentors at the concentration of 1 g/l, 5 g/l and 10 g/l respectively under the same conditions as above. No increasing effect of any of the T-A2 major components ratios was observed.

EXAMPLE 3

*Actinoplanes teichomyceticus* nov. sp. ATCC 31121 was pre-cultivated as described in Example 2. The flasks of the preculture were used to inoculate a jar fermentor containing 10 liters of the nutrient medium reported in Example 2.

The fermentor was incubated aerobically under stirring at 25° C. for 24 hours and then 2 g/l L-valine were added. The L-valine had previously been dissolved in water (2 g/15 ml) by adding sulfuric acid to reach pH 3 and the obtained solution had been stirred at 120° C. for 10 minutes.

The fermentation was continued at 25° C. for further 50 hours then the fermentor was harvested.

The broth filtered at pH 11 and analyzed according to the procedure described in Example 1, contained 220 microgram/l of T-A2 having the following composition: T-A2-1: 2%; T-A2-2: 95%, T-A2-3: 3%.

We claim:

1. A process for preparing teicoplanin $A_2$ (T-A2) selectively enriched in one of its major components, wherein said component is T-A2-1, which comprises adding to the culture medium of *Actinoplanes teichomyceticus* nov. sp. ATCC 31121, or one of its mutant which produces T-A2-1 through the same metabolic pathway, an effective amount of an appropriate precursor of the acyl group of the glucosamine moiety of T-A2-1, wherein said appropriate precursor is selected from the group consisting of:

linoleic acid, its salts with bases which are non-toxic to the microorganism and its esters with mono- and poly-hydroxy lower alkanols.

2. A process for preparing teicoplanin A$_2$ (T-A2) selectively enriched in one of its major components, wherein said component is T-A2-2, which comprises adding to the culture medium of *Actinoplanes teichomyceticus* nov. sp. ATCC 31121, or one of its mutant which produces T-A2-2 through the same metabolic pathway, an effective amount of an appropriate precursor of the acyl group of the glucosamine moiety of T-A2-2, wherein said appropriate precursor is selected from the group consisting of:

valine, its salts with acid and bases which are non-toxic to the microorganism, alpha-keto-isovaleric acid, its salts with bases which are non-toxic to the microorganism its esters with mono- and poly-hydroxy lower alkanols, isobutyric acid, its salts with bases which are non-toxic to the microorganism, its esters with mono- and poly-hydroxy lower alkanols, and isobutanol and its esters with acids which are non-toxic to the microorganism.

3. A process for preparing teicoplanin A$_2$ (T-A2) selectively enriched in one of its major components, wherein said component is T-A2-3, which comprises adding to the culture medium of *Actinoplanes teichomyceticus* nov. sp. ATCC 31121, or one of its mutant which produces T-A2-3 through the same metabolic pathway, an effective amount of an appropriate precursor of the acyl group of the glucosamine moiety of T-A2-3, wherein said appropriate precursor is selected from the group consisting of:

oleic acid, its salts with bases which are non-toxic to the microorganism, and its esters with mono- and poly-hydroxy lower alkanols.

4. A process for preparing teicoplanin A2 (T-A2) selectively enriched in one of its major components, wherein said component is T-A2-4, which comprises adding to the culture medium of *Actinoplanes teichomyceticus* nov. sp. ATCC 31121, or one of its mutant which produces T-A2-4 through the same metabolic pathway, an effective amount of an appropriate precursor of the acyl group of the glucosamine moiety of T-A2-4, wherein said appropriate precursor is selected from the group consisting of:

isoleucine, its salts with acids and bases which are non-toxic to the microorganism, alpha-keto-beta-methylvaleric acid, its salts with bases which are non-toxic to the microorganism, its esters with mono- and poly-hydroxy lower alkanols, 2-methylbutyric acid, its salts with bases which are non-toxic to the microorganism, its esters with mono- and poly-hydroxy lower alkanols, and 2-methylbutanol and its esters with acids which are non-toxic to the microorganism.

5. A process for preparing teicoplanin A2 (T-A2) selectively enriched in one of its major components, wherein said component is T-A2-5, which comprises adding to the culture medium of *Actinoplanes teichomyceticus* nov. sp. ATCC 31121, or one of its mutant which produces T-A2-5 through the same metabolic pathway, an effective amount of an appropriate precursor of the acyl group of the glucosamine moiety of T-A2-5, wherein said appropriate precursor is selected from the group consisting of:

leucine, its salts with acids and bases which are non-toxic to the microorganism, isovaleric acid, its salts with bases which are non-toxic to the microorganism, its esters with mono- and poly-hydroxy lower alkanols, alpha-keto-isocaproic acid, its salts with bases which are non-toxic to the microorganism, its esters with mono- and poly-hydroxy lower alkanols, and isoamyl alcohol and its esters with acids which are non-toxic to the microorganism.

6. A process as claimed in claim 1 wherein the appropriate precursor added is linoleic acid or its salts with bases non-toxic to the microorganism and the effective amount ranges between 0.1 g/l and 2.5 g/l.

7. A process as claimed in claim 1 wherein the appropriate precursor added is an ester of linoleic acid with a mono- or poly-hydroxy lower alkanol and the effective amount ranges between 0.5 g/l and 15 g/l.

8. A process as claimed in claim 2 wherein the appropriate precursor added is valine or its salts with acids and bases non-toxic to the microorganism and the effective amount ranges between 0.5 g/l and 5 g/l.

9. A process as claimed in claim 2 wherein the appropriate precursor added is isobutyric acid or its salts with bases non-toxic to the microorganism and the effective amount ranges between 0.1 g/l and 2.5 g/l.

10. A process as claimed in claim 2 wherein the appropriate precursor added is an ester of isobutyric acid with a mono- or poly-hydroxy lower alkanol and the effective amount ranges between 0.5 g/l and 15 g/l.

11. A process as claimed in claim 2 wherein the appropriate precursor added is isobutanol or its esters with acids non-toxic to the microorganism and the effective amount ranges between 0.5 g/l and 5 g/l.

12. A process as claimed in claim 3 wherein the appropriate precursor added is oleic acid or its salts with bases non-toxic to the microorganism and the effective amount ranges between 0.1 g/l and 2.5 g/l.

13. A process as in claim 3 wherein the appropriate precursor added is an ester of oleic acid with a mono- or poly-hydroxy lower alkanol and the effective amount ranges between 0.5 g/l and 15 g/l.

14. A process as claimed in claim 4 wherein the appropriate precursor added is isoleucine or its salts with acids and bases non-toxic to the microorganism and the effective amount ranges between 0.5 g/l and 5 g/l.

15. A process as claimed in claim 4 wherein the appropriate precursor added is 2-methylbutyric acid or its salts with bases non-toxic to the microorganism and the effective amount ranges between 0.1 g/l and 2.5 g/l.

16. A process as claimed in claim 4 wherein the appropriate precursor added is an ester of 2-methylbutyric acid with a mono- or poly-hydroxy lower alkanol and the respective selectively effective amount ranges between 0.5 g/l and 15 g/l.

17. A process as claimed in claim 4 wherein the appropriate precursor added is 2-methylbutanol or its ester with an acid non-toxic to the microorganism and the effective amount ranges between 0.5 g/l and 5 g/l.

18. A process as claimed in claim 5 wherein the appropriate precursor added is leucine or its salts with acids and bases non-toxic to the microorganism and the effective amount ranges between 0.5 g/l and 5 g/l.

19. A process as claimed in claim 5 wherein the appropriate precursor added is isovaleric acid or its salts with bases non-toxic to the microorganism and the effective amount ranges between 0.1 g/l and 2.5 g/l.

20. A process as claimed in claim 5 wherein the appropriate precursor added is an ester of isovaleric acid with a mono- or poly-hydroxy lower alkanols and the effective amount ranges between 0.5 g/l and 15 g/l.

21. A process as claimed in claim 5 wherein the appropriate precursor added is isoamyl alcohol or its esters with acids non-toxic to the microorganism and the effective amount ranges between 0.5 g/l and 5 g/l.

22. A process as claimed in claim 1 wherein the appropriate precursor added is alpha-keto-isovaleric acid, its salts with bases non-toxic to the microorganism or its esters with mono- or poly-hydroxy lower alkanols and the effective amount ranges between 0.5 g/l and 5 g/l.

23. A process as claimed in claim 4 wherein the appropriate precursor added is alpha-keto-beta-methylvaleric acid, its salts with bases non-toxic to the microorganism or its esters with mono- or poly-hydroxy lower alkanols and the effective amount ranges between 0.5 g/l and 5 g/l.

24. A process as claimed in claim 5 wherein the appropriate precursor added is alpha-keto-isocaproic acid, its salts with bases non-toxic to the microorganism, or its esters with mono- or poly-hydroxy lower alkanols and the effective amount ranges between 0.5 g/l and 5 g/l.

25. A process according to claim 6 wherein the effective amount ranges between 0.3 g/l and 1.5 g/l.

26. A process according to claim 7 wherein the effective amount ranges between 1 g/l and 5 g/l.

27. A process according to claim 8 wherein the effective amount ranges between 1 g/l and 3 g/l.

28. A process according to claim 9 wherein the effective amount ranges between 0.3 g/l and 1.5 g/l.

29. A process according to claim 10 wherein the effective amount ranges between 1 g/l and 5 g/l.

30. A process according to claim 11 wherein the effective amount ranges between 1 g/l and 2 g/l.

31. A process according to claim 12 wherein the effective amount ranges between 0.3 g/l and 1.5 g/l.

32. A process according to claim 13 wherein the effective amount ranges between 1 g/l and 5 g/l.

33. A process according to claim 14 wherein the effective amount ranges between 1 g/l and 3 g/l.

34. A process according to claim 15 wherein the effective amount ranges between 0.3 g/l and 1.5 g/l.

35. A process according to claim 16 wherein the effective amount ranges between 1 g/l and 5 g/l.

36. A process according to claim 17 wherein the effective amount ranges between 1 g/l and 2 g/l.

37. A process according to claim 18 wherein the effective amount ranges between 1 g/l and 3 g/l.

38. A process according to claim 19 wherein the effective amount ranges between 0.3 g/l and 1.5 g/l.

39. A process according to claim 20 wherein the effective amount ranges between 1 g/l and 5 g/l.

40. A process according to claim 21 wherein the effective amount ranges between 1 g/l and 2 g/l.

41. A process according to claim 22 wherein the effective amount ranges between 1 g/l and 3 g/l.

42. A process according to claim 23 wherein the effective amount ranges between 1 g/l and 3 g/l.

43. A process according to claim 24 wherein the effective amount ranges between 1 g/l and 3 g/l.

44. A process according to claim 1, 2, 3, 4, or 5 wherein *Actinoplanes teichomyceticus* nov. sp. ATCC 31121 is utilized.

45. A process as claimed in any one of the claims 6, 8, 9, 12, 14, 15, 18, 19, 22, 23 and 24 where the salts with bases non-toxic to the microorganism are sodium or ammonium salts.

46. A process as claimed in any one of the claims 26, 29, 32, 35, 39, 41, 42 and 43 wherein the ester is an ester with one of the following alkanols: methanol, ethanol, propanol, ethylene glycol and glycerol.

47. A process as claimed in any one of the claims 27, 33 and 37 wherein the aminoacid is in the L-form.

48. A process as claimed in any one of the claims 30, 36 and 40 wherein the ester with an acid non-toxic to the microorganism is an ester with one of the following acids: acetic acid, propionic acid and butyric acid.

49. A process as claimed in any one of the claims 6, 7, 12 and 13 wherein the unsaturated fatty acids or their esters are added as natural raw materials containing said acids or their glycerides.

* * * * *